United States Patent

Broderick et al.

[11] Patent Number: 5,156,626
[45] Date of Patent: Oct. 20, 1992

[54] SET OF PROVISIONAL PROSTHESIS INSTRUMENTATION

[75] Inventors: Melissa A. Broderick; Nisra Thongpreda; Joseph S. Presti, all of Warsaw, Ind.

[73] Assignee: Zimmer, Inc., Warsaw, Ind.

[21] Appl. No.: 546,116

[22] Filed: Jun. 29, 1990

[51] Int. Cl.$^5$ .............................................. A61F 2/32
[52] U.S. Cl. ...................................... 623/22; 623/16; 623/18; 623/23
[58] Field of Search ....................... 606/90, 99; 623/22

[56] References Cited

U.S. PATENT DOCUMENTS

| | | | |
|---|---|---|---|
| 3,813,699 | 6/1974 | Giliberty | 3/1 |
| 4,135,517 | 1/1979 | Reale | 128/303 R |
| 4,241,463 | 12/1980 | Khovaylo | 3/1.913 |
| 4,528,980 | 7/1985 | Kenna | 128/92 EB |
| 4,676,799 | 6/1987 | Legrand | 623/22 |
| 4,716,894 | 1/1988 | Lazzeri et al. | 606/99 |
| 4,718,911 | 1/1988 | Kenna | 623/22 |
| 4,770,658 | 9/1988 | Geremakis et al. | 623/22 |
| 4,960,427 | 10/1990 | Noiles | 623/22 |

OTHER PUBLICATIONS

Biomet, Bi-Polar Articulating Hip System and Bio-Moore Modular Endoprosthesis System, Aug., 1985.
Biomet, Inc. publication—Bio-Moore Modular Endoprosthesis System—Aug. 1985.
Biomet, Inc. Publication—Bi-Polar Articulating Hip System—no date available.
Howmedica publication—Centrax Bipolar System—1987.
Howmet Corporation—Cup Template for MacBride and McGoey-Evans Cups—1969.
Orthopaedic Device Corporation publication—Endo Head-Neck Extension 3M publication—Bateman UPF Universal Proximal Femur—No date available.
Zimmer, Inc. publication—Zimmer Endoprostheses—Lit. No. 83-001-4005-0242—1983.
Zimmer, Inc. publication—Universal Acetabular Provisionals—May 6, 1988.
Zimmer, Inc. publication—BIAS Total Hip System Surgical Technique (pp. 10-12, 32, 33)—1986.

*Primary Examiner*—David Isabella
*Assistant Examiner*—Gina Gualtieri
*Attorney, Agent, or Firm*—Margaret L. Geringer

[57] ABSTRACT

A set of provisional prosthesis instrumentation including an outer shell component, a first inner component, and a second inner component different from the first inner component. The first inner component comprises a substantially hemispherical interior surface therein, while the second inner component comprises a non-hemispherical, truncated cone or a nonhemispherical, substantially cylindrical surface therein. Either the first inner component style or the second inner component style may be selectively inserted into the shell component. The first and second inner components (inserts) are releasably connectable with the shell. The first style inner component may typically be used as a provisional for a bipolar prosthesis for a hemiarthroplasty procedure, while the second style of inner component may typically be used as a unipolar endoprosthesis provisional for a hemiarthroplasty procedure. The same style of shell component is utilized for both styles of inner components. A plurality of sizes for the shell component and for the first inner component and for the second inner component may be provided for selective utilization. The shell component may also be used in conjunction with a handle as a sizer instrument.

13 Claims, 3 Drawing Sheets

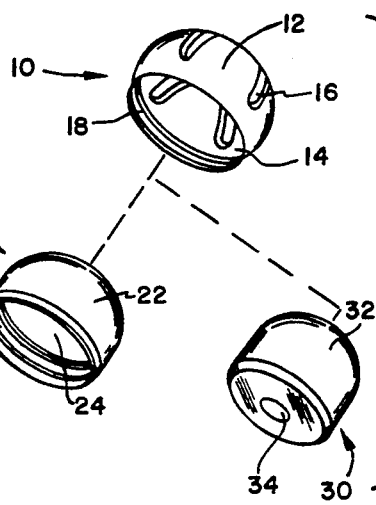
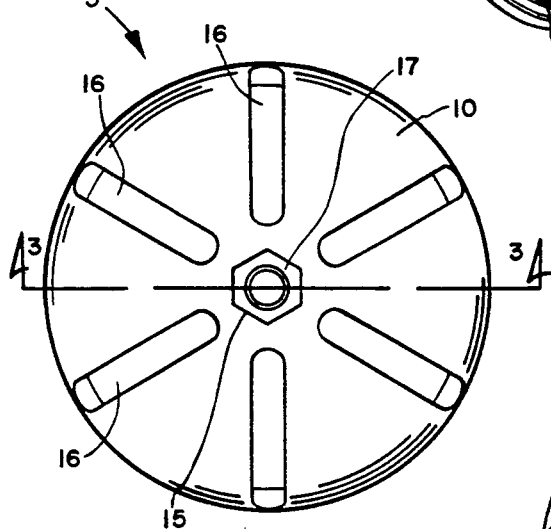
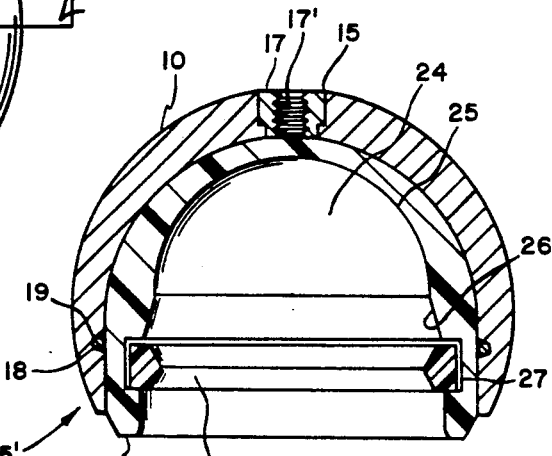
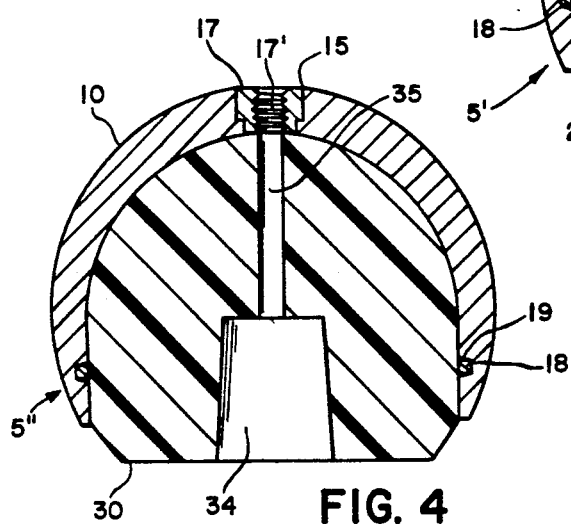

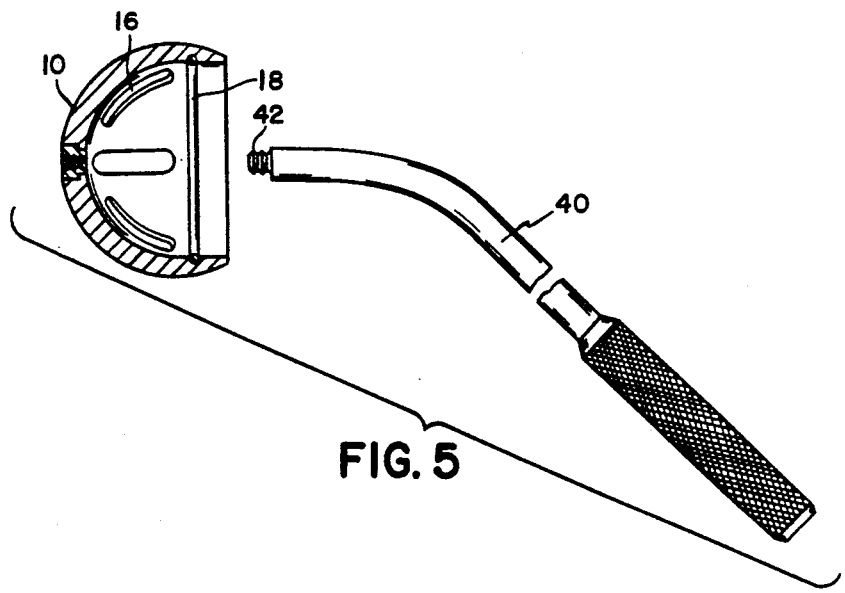
FIG. 5
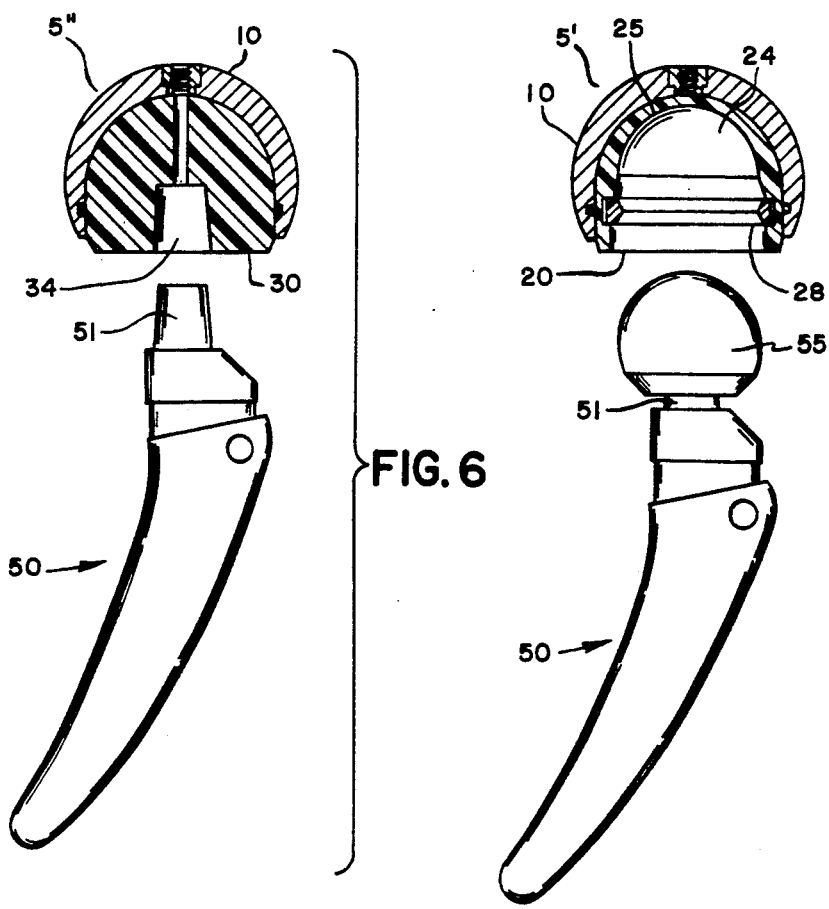
FIG. 6
FIG. 7 ps
5,156,626

SET OF PROVISIONAL PROSTHESIS INSTRUMENTATION

BACKGROUND OF THE INVENTION

The present invention relates to a set of provisional prosthesis instrumentation, and more particularly to provisional instrumentation which is suitable for use in hip hemiarthroplasty procedures in which the proximal portion of the femur is replaced with a suitable prosthetic hip joint implant or implant assembly which will mate or articulate directly with the natural acetabulum (as opposed to mating with a prosthetic acetabular joint implant component).

Two different types of procedures are typically suitable for hemiarthroplasty procedures. One of these types is the use of a bipolar prosthesis member such as those described in U.S. Pat. No. 3,813,699 to Giliberty or U.S. Pat. No. 4,770,658 to Geremakis et al. In general, a bipolar prosthesis has an external surface which articulates with the natural acetabulum and an internal surface which articulates with the spherical head member of a prosthetic femoral component. The other of these types is often referred to as a unipolar endoprosthesis in which the prosthetic femoral component includes a spherical head member which is large enough to articulate directly with the natural acetabulum. Both of the above hemiarthroplasty procedures enable articulation with the natural acetabulum. These two procedures permit later conversion to a total hip replacement in which the acetabular portion is also replaced with a prosthetic acetabular component. With the bipolar procedure, the bipolar prosthesis is removed from the head of the hip stem, and an acetabular prosthesis implanted which mates with the head of the remaining femoral component. With the unipolar endoprosthesis, these may typically be modular (where the head is a separate component from the stem portion of the hip prosthesis). This permits the larger unipolar head to be removed and replaced with a smaller head without removing the femoral stem to enable this smaller head to mate with an acetabular prosthetic implant component Various types of provisional or trial prosthesis instrumentation are typically used in a femoral prosthesis surgical procedure to enable the surgeon to test the fit of a prosthesis with the trial components before actual implantation of the prosthesis. An example of a femoral prosthesis trial fitting device is described in U.S. Pat. 4,135,517 to Reale. This patent discloses a trial head 30 and a bearing insert which removably fits within the trial head. The bearing insert may be removably mountable on either a femoral prosthesis stem or a trial handle. Different sized trial heads may be utilized with this device.

Many provisional hip components utilize a single or one-piece provisional portion which is fitted to the spherical head of a hip stem implant or trial stem. Various sized single provisional portions are available. Such a provisional system is sold by Zimmer, Inc. for use with their BiArticular II Hip (a bipolar prosthesis). The BiArticular II Hip Prosthesis corresponds to the U.S. Pat. No. 4,770,658 to Geremakis et al., identified above.

In addition to utilizing a trial prosthesis, it is typical to utilize an acetabular sizing instrument for properly determining the size of the acetabulum. An example of such an instrument is disclosed in U.S. Pat. No. 4,528,980 to Kenna which includes an acetabular sizer which includes viewing ports in the shell for visual inspection of the acetabulum while the shell is seated therein.

OBJECTS OF THE INVENTION

A principle object of this invention is to provide a set of provisional hip instruments which includes an outer shell component which can be utilized with two different types of inner components, for two different types of surgical procedures.

Another object of the invention is to provide a set of surgical hip instrumentation in which a single style outer shell component can be removably fitted with a first style inner (insert) component for use as a bipolar prosthesis provisional or with a second style inner (insert) component for use as a unipolar endoprosthesis for hemiarthroplasty.

A further object of the invention is to provide such a shell component which can also be used as an acetabular sizing gauge.

A still further object of the invention is to provide a set of provisional hip instrumentation in which a common style outer shell component can be used with two different interchangeable styles of inner (insert) components for two different types of surgical procedures in order to reduce inventory.

A further object of the invention is to provide a plurality of sizes of shell components and a plurality of sizes of mating inner components of both a first style and a different second style.

SUMMARY OF THE INVENTION

The present invention provides a set of provisional prosthesis instrumentation including an outer shell component, a first inner component, and a second inner component different from the first inner component. In a particularly advantageous embodiment, the first inner component comprises a substantially hemispherical interior surface therein, while the second inner component comprises a nonhemispherical, truncated cone or a nonhemispherical, substantially cylindrical surface therein. Either the first inner component style or the second inner component style may be selectively inserted into the shell component. The first and second inner components are releasably mateable/insertable with the shell. The first style inner component may typically be used as a provisional for a bipolar prosthesis for a hemiarthroplasty procedure, while the second style of inner component may typically be used as a unipolar endoprosthesis provisional for a hemiarthroplasty procedure. The same style of shell component is utilized for both styles of inner components. A plurality of sizes for the shell component and for the first inner component and for the second inner component may be provided for selective utilization. The shell component may also be used in conjunction with a handle as a sizer instrument.

BRIEF DESCRIPTION OF THE DRAWINGS

These features and objects of the invention, as well as others, will become apparent to those skilled in the art by referring to the accompanying drawings:

FIG. 1 is an exploded perspective view of a shell component, a first inner component, and a second inner component according to the present invention;

FIG. 2 is a top view of the shell component of FIG. 1 assembled with one of the inner components inserted therein;

FIG. 3 is a cross-sectional view of the shell assembled with the first inner component taken along lines 3—3 of FIG. 2;

FIG. 4 is a cross-sectional view of the shell assembled with the second inner component taken along lines 3—3 of FIG. 2;

FIG. 5 is an exploded view, including a cross-sectional view of the shell only taken along lines 3—3 of FIG. 2, shown with a side view of the handle;

FIG. 6 is an exploded view, including a cross-sectional view of the shell assembled with the second inner component taken along lines 3—3 of FIG. 2, shown with a side view of a corresponding provisional hip stem;

FIG. 7 is an exploded view including a cross-sectional view of the shell assembled with the first inner component taken along lines 3—3 of FIG. 2, shown with a side view of a corresponding provisional hip stem and related provisional head;

DETAILED DESCRIPTION OF THE INVENTION

Figure 8:
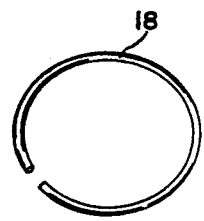
FIG. 8 is a perspective view of the split ring member of the first inner component of FIG. 3.

FIGS. 1-10 illustrate a particularly advantageous embodiment of a set of provisional prosthesis instrumentation. The invention will be described with reference to instrumentation for the hip joint, and is particularly suited as such. However, it is understood that the principles of the invention may be suitable and applicable for other joints, such as the shoulder or the like.

The set of provisional prosthesis instrumentation 1, such as is suitable for use with a hemiarthroplasty femoral hip replacement, includes an outer shell component 10, a first inner component 20, and a second inner component 30 different from the first inner component 20. The outer shell 10 includes an exterior surface 12 and an interior surface 14. The first inner component includes an exterior surface 22, which is shaped to correspondingly mate with the interior surface 14 of the shell component 10, and an interior surface 24 having a first configuration therein. The second inner component 30 includes an exterior surface 32, which is also shaped to correspondingly mate with the interior surface 14 of the shell component 10, and an interior surface having a second configuration therein different from the first configuration of the first inner component 20. Either the first inner component 20 or the second inner component 30 is selectively inserted into the outer shell component 10 in mating contact with the interior surface 14 of shell component 10. Thus, the first inner component 20 and second inner component 30 are interchangeable and each mate respectively with outer shell component 10.

The combination of the outer shell component 10 and either one of the first or second inner components is designated as assembly 5. If shell 10 is assembled with first inner component 20, it is designated as assembly 5', and if shell 10 is assembled with the second inner component 30, it is designated as assembly 5".

The first configuration of the interior surface 24 of the first inner component 20 includes a substantially hemispherical surface 25 therein This hemispherical surface 25 enables the first inner component 20 to mate with a corresponding spherical provisional head member 55 which is shown in FIG. 7. The provisional head 55 is attached to a corresponding provisional hip stem 50 via neck 51 on stem 50. It is noted that the provisional or trial first inner component 20 in combination with a corresponding provisional or trial shell component may be utilized for trial fitting with the natural acetabulum during surgery in conjunction with such a trial provisional stem 50 and provisional head 55 combination as shown in FIG. 7, or the first inner component 20 and shell component 10 assembly could be used with the actual implant stem and head (not shown). Thus, the assembly 5' (shown in FIGS. 3 and 7) which includes shell 10 and first inner component 20, is utilized as a provisional in conjunction with a bipolar surgical procedure.

Figure 9:
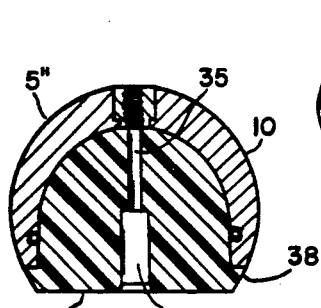
FIG. 9 is a cross-sectional view of the shell assembled with an alternate embodiment of the second inner component taken along lines 3—3 of FIG. 2.
Figure 10:
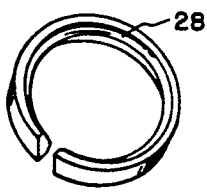
FIG. 10 is a perspective view of the split ring member of the shell component of FIG. 1.

The second configuration of the interior surface 34 of the second inner component 30 includes a nonhemispherical truncated cone as designated by 34 in FIGS. 4 and 6 or a nonhemispherical substantially cylindrical surface as designated by 34' on alternate second inner component 30' in FIG. 9. This nonhemispherical truncated cone-shaped interior surface 34 enables the second inner component 30 to mate with a provisional hip stem 50 via corresponding truncated cone-shaped neck 51 on stem 50 as shown in FIG. 6. The nonhemispherical, substantially cylindrical interior surface 34' enables the alternate second inner component 30' to mate with a provisional hip stem via a corresponding substantially cylindrical shaped neck (not shown) on the stem. It is noted that the provisional or trial second inner component 30 or 30' in combination with a corresponding provisional or trial shell component 10 may be utilized for trial fitting with the natural acetabulum during surgery in conjunction with such a trial or provisional stem 50, such as shown in FIG. 6 or the second inner component 30 and shell component 10 assembly could be used with the actual implant stem (not shown). Thus, the assembly 5" (shown in FIGS. 4, 6, and 9) which includes shell 10 and second inner components 30 and 30', is utilized as a provisional in conjunction with a unipolar surgical procedure. It is noted that both second inner components 30 and 30' include a channel 35 therethrough connecting the inner surface 34 or 34', respectively, with exterior surface 32. The channel 35 allows fluid or air to be released therethrough.

The set of provisional instrumentation 1 may include a plurality of shell components 10 of varying sizes, a plurality of first inner components of varying sizes, and a plurality of second components of varying sizes. The varying sizes are not shown in the Figs., but it is understood that sizing may vary and that mating components have corresponding/mating sizing features as desired.

Prior to the use of the provisional assembly 5 for trial fitting with the acetabulum, the correct size outer shell component 10 must be selected. The exterior surface 12 of shell 10 includes a hemispherical portion of a sphere, although more than half of a sphere may be provided, as shown in the Figs. It is important to match the exterior shape of shell 10 as accurately as possible with the shape of the natural acetabulum.

The shell 10 includes a central hole 15 with a nut 17 located in hole 15. The nut 17 includes internal threads 17' therein. The nut 17 may be press-fit into hole 15. A handle 40, as shown in FIG. 5, with threaded tip 42 is threaded into a selected size shell 10 from the interior surface 14 of the shell 10 and into the threaded nut 17. The shell 10 is then positioned against the acetabulum (not shown) to observe the fit therebetween. A plurality of elongated slots 16 are provided in the shell 10 therethrough to aid in visualization of the contact of the shell 10 with the acetabulum. If there is not good mating contact with the shell 10 and acetabulum, another shell 10 with a different size exterior surface 12 is selected. This process is continued until a shell 10 with the desired fit between the exterior surface 12 and the acetabulum is determined.

The cross-sectional shape of the interior surface 14 of shell 10 and the exterior surfaces 22 and 32 of both the first and second inner components 20 and 30, respectively, may be substantially U-shaped, as shown in FIGS. 3 and 4, although any suitable corresponding, mating interior surface 14 and exterior surface 22 or 32 may be utilized. The corresponding interior surface 14 and exterior surfaces 22 and 32 are sized to slide releasably in and out in frictional engagement with each other, with a slip-fit or friction fit between the shell 10 and inner component 20 or 30. Manual pressure is preferably all that is required to slide the inner component 20 or 30 into or out of shell 10. Finger pressure will connect the inner components 20 or 30 with the corresponding shell 10. To disassemble the first inner component 20 from shell 10, the shell 10 is held while the interior surface 24 of the inner component 20 is gripped with finger pressure and pulled out. Depending on the size of the interior surface 34 of the second inner component 30, it may be difficult to grip in this manner, thus it is recommended that a blunt instrument (not shown) may be used to push the inner component 30 out of shell 10 by inserting the blunt instrument through a slot 16. This method may also be used to disassemble the first inner component 20 and shell 10, if desired.

The shell 10 may include a circular groove 19 about the interior surface 14 as shown in FIGS. 3 and 4. A resilient split ring 18 (refer also to FIG. 10) is retained in the groove 19 and maintained by a biased spring force. The split ring 18 is expandable and thus recedes further into the groove upon insertion of an internal component 20 or 30. The frictional pressure of resilient split ring 18 against the exterior surface 22 or 32 of inner components 20 or 30, respectively, helps to maintain the inner component 20 or 30 in shell 10 until the user slides the inner component 20 or 30 back out to release it from the shell 10. It is also noted that the inner component, such as with the alternate second inner component 30' shown in FIG. 9, may include a protruding peripheral lip or rim 38. The rim 38 may be used on an inner component/insert 20 or 30 that is for use with a thicker shell 10 to provide a smooth transition between the inner component/insert 20 or 30 and such shell 10. Inserts that fit within thinner shells, such as shown in FIGS. 3 and 4, typically do not have a rim. The rim 38, as shown in FIG. 9, does not protrude beyond the edge of shell 10.

It s noted that the first inner component 20 may have a chamfer 26 flaring outwardly from hemispherical surface 25, which leads into recessed area 27. The recessed area 27 is bound by upper and lower edges which retain a resilient split 28 ring therein the recessed area 27. The resilient ring expands and thus recedes into the recessed area 27 upon insertion of provisional spherical head member 55 (or the like spherical implant head member, not shown). Once the head passes split ring 28 the resilient ring contracts to its rest position capturing the head 55 in first inner component 20. The inner surface of the split ring 28 has a dual chamfer as shown in FIGS. 3, 7, and 8 to assist in expansion of the ring 28 upon insertion and removal of head 55 from first inner component 20. Again, manual pressure is preferably all that is required to insert and remove the head 55 from provisional inner component 20.

The interior surface 34 of second provisional inner component 30 is dimensioned to releasably fit over correspondingly-shaped neck 51.

In use, the surgeon determines whether he will be doing a bipolar prosthesis hemiarthroplasty procedure (in which case he would want to use shells 10 and first inner components 20) or a unipolar prosthesis hemiarthroplasty procedure (in which case he would want to use shells 10 and second inner components 30). Again, the present invention enables the user to use a common style outer provisional shell 10 with two different, interchangeable styles of inner provisional components, each adapted for a different type of surgical procedure. This same outer shell 10 which is used with the provisional assembly 5, can be used without an inner component, but with an acetabular gauge handle to size the natural acetabulum. In use, the surgeon would selectively attach the handle 40 first to one size (and potentially to several different sizes) of shells 10 to determine and thus select the appropriate size shell component. Then the handle is detached from the selected shell 10. The desired mating size of either the first inner component or the second inner component is selected, depending on the desired surgery to be performed. The selected inner component is then inserted into the selected shell component for use in a provisional or trial fitting.

If first inner component 20 is selected for use with shell 10 for a bipolar trial fitting, this provides trial dual joint articulation, with articulation about exterior surface 12 of shell 10 (against the natural acetabulum) and with articulation about interior surface 24 of first inner component 20 (about head 55). Alternatively, if second inner component 30 is selected for use with shell 10 for a unipolar trial fitting for a hemiarthroplasty procedure, this provides trial single joint articulation, with articulation about exterior surface 12 of shell 10 only (against the natural acetabulum).

Figure 11:
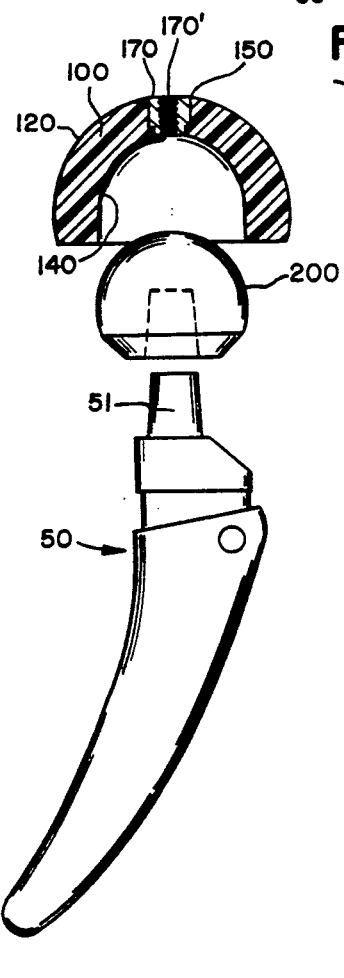
FIG. 11 is an exploded view, including a cross-sectional view of an alternate embodiment of the shell, shown with a side view of an alternate embodiment of the first component and with a side view of a corresponding provisional hip stem.
Figure 12:
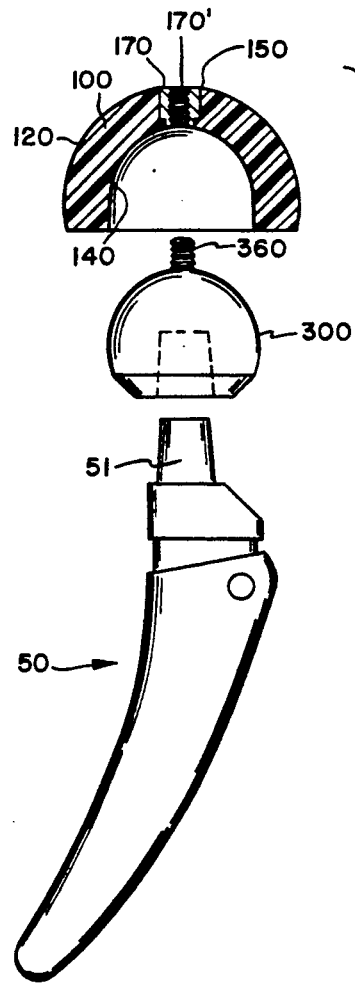
FIG. 12 is an exploded view, including a cross-sectional view of an alternate embodiment of the shell, shown with a side view of an alternate embodiment of the second component and with a side view of a corresponding provisional hip stem.

FIGS. 11–12 illustrate an alternative embodiment for a set of provisional prosthesis instrumentation in which a common style outer shell can be selectively used with either of two different interchangeable styles of inner components, one for use with bipolar surgery and the other for use with unipolar surgery for hemiarthroplasty. In FIGS. 11–12, the outer shell 100 includes exterior surface 120 and interior surface 140. Shell 100 includes central hole 150 with nut 170, including threads 170'. The shell 100 of FIGS. 11–12 may also be used as a sizing gauge, as described previously for shell 10. However, shell 100 may be relatively thicker than shell 10 and includes a substantially hemispherical interior surface 140. Accordingly, first inner component 200, for use in a bipolar procedure, corresponds to a substantially spherical member (such as a provisional head or an implant femoral head) which mates directly with interior shell surface 140. Since the first inner component 200 corresponds to a substantially spherical member, it is noted that if the diameter of the first inner component 200 in FIG. 11 is similar to the diameter of head 55 of the embodiment in FIG. 7 and if the outer diameter of shell 100 of FIG. 11 is similar to the outer diameter of shell 10 of the embodiment in FIG. 7, it follows that the thickness of shell 100 of FIG. 11 would be relatively thicker than shell 10 of FIG. 7, with the thickness of shell 100 of FIG. 11 being substantially similar to the combined thickness of shell 10 and first inner component 20 of FIG. 7. First inner component 200 is fitted to a provisional hip stem 50 or implant stem (not shown). Thus, trial fitting provides dual joint articulation about exterior shell surface 120 and about the exterior of first inner component 200 with interior shell surface 140. The second inner component 300 includes a substantially hemispherical surface to mate with interior shell surface 140, and also includes a threaded post 360 extending therefrom. Post 360 may be threadedly engaged with threaded nut 170 which thus prevents articulation between second inner component 300 and shell 100. Other engaging means to secure the post 360 to the shell to prevent articulation between shell 100 and second component 300 could be used. Thus, when second inner component 300, for use in a unipolar hemiarthroplasty procedure, is selectively inserted/mated with shell 100, and also fitted to a provisional hip stem 50 or implant stem (not shown), trial fitting provides single joint articulation about the exterior shell surface 120 only.

The components of the present invention are made in accordance with any suitable manufacturing practices. Additionally, any suitable materials for provisional prosthetic instrumentation may be utilized. Examples of such suitable materials are, the first and second inner components 20 and 30 and ring 28 may be made out of a plastic, such as polyetherimide, while the shell 10 may be made out of aluminum, and the ring 18, nut 17, and handle 40 may be made out of stainless steel or other suitable metal. With the alternate embodiment of FIGS. 11 and 12, the shell 100 and first and second inner components 200 and 300 may each be made out of a plastic, or any other suitable material. It is understood that any suitable material may be utilized for any of the components.

The various sizes of shells 10 and inner and outer components 20 and 30 may vary in accordance with the surgical needs. For example, the outer shells 10 may be provided with various external diameters. External diameters typically may run incrementally from 38 mm to 72 mm, although the sizes are not limited thereto. The external diameter of the various sizes of shells 10 correspond to the various sizes of the outer diameters of the bipolar implant components (not shown) or to the various sizes of the outer diameter of the unipolar endoprosthesis heads (not shown), which are to be selected for implantation. In general, the sizing of trial prostheses is designed to correlate with the corresponding prosthetic components to be implanted. The inner hemispherical surface 25 of first inner component 20 may vary in accordance with the corresponding sizes of spherical head members with which it will mate. Examples of typical size ranges for the diameter for the inner hemispherical surface 25 are 22 mm, 28 mm and 32 mm, although the sizing is not limited thereto. The inner surface 34 or 34' for either second inner component 30 or 30', respectively, is basically sized to releasably slide on and off a corresponding neck member of a stem such as 50. The interior of the various shells 10 are sized and shaped to correspond with the exteriors of any mating sizes of inner components 20 or 30.

The chart below identifies a set of provisional instrumentation in according with the embodiment of FIGS. 1–10 as a representative sizing scheme. The inner components 20 or 30 listed across from each respective shell 10 are sized to correspondingly mate together. For example, a shell 10 with an interior surface 14 having an inner size A corresponds and mates with inner components 20 or 30 having an exterior surface 22 or 32, respectively, having an outer size A. The dimensions of inner size A and outer size A are suitably designed to releasably mate together, as previously described. Accordingly, inner size B mates with outer size B, inner size C with outer size C, and inner size D with outer size D. To assist the user, the various inner shells 10 and inner components 20 or 30 may be color-coded. For example, the inner size A and outer size A components could all be gold, so that any gold inner component 20 or 30 will mate correctly with any gold shell 10. Accordingly, all size B's could be black, all size C's could be gray, while all size D's could be blue. It is understood that the color-coding could be varied as desired. Also, it is noted that the specific identified or suggested potential mating combinations on the chart are intended to correlate with suitable corresponding implant systems (specific implant systems not shown). For example, the second inner component 30 having outer size D is indicated on the chart to mate with the 60 and 63 mm shell components 10 having inner size D. However, since any outer size D component could mate with any inner size D component, it is understood that the outer size D inner component 30 could actually mate with the other inner size D shells too; but this is not listed on the chart as a recommended combination for the particular representative sizing scheme for the corresponding implant system. It is understood that the invention is not limited to the particular sizing scheme identified below.

| Shell Component 10 (Outer diameter size in mm) | First Inner Component 20 (For a bipolar provisional) | Second Inner Component 30 (For a unipolar provisional) |
| --- | --- | --- |
| 38 mm (Inner size A) | .Outer Size A (22 mm I.D.) (Mates with 40, 41, 42, 43 mm shells) | .Outer Size A (Mates with 38, 40, 41, 42, 43 mm shells) |
| 40 mm (Inner size A) | | |
| 41 mm (Inner size A) | | |
| 42 mm (Inner size A) | | |
| 43 mm (Inner size A) | | |
| 44 mm (Inner size B) | .Outer Size B (28 mm I.D.) (Mates with 44, 45, 46, 47, 48, 49 mm shells), or .Outer Size B (32 mm I.D.) (Mates with 47, 48, 49 mm shells) | .Outer Size B (Mates with 44, 45, 46, 47, 48, 49 mm shells) |
| 45 mm (Inner size B) | | |
| 46 mm (Inner size B) | | |
| 47 mm (Inner Size B) | | |
| 48 mm (Inner Size B) | | |
| 49 mm (Inner Size B) | | |
| 50 mm (Inner Size C) | .Outer Size C (28 mm I.D.) (Mates with 50, 51, 52, 53, 54, 55, 57, 58 mm shells), or .Outer Size C (32 mm I.D.) (Mates with 50, 51, 52, 53, 54, 55, 57, 58 mm shells) | .Outer Size C (Mates with 50, 51, 52, 53, 54, 55, 56, 57 mm shells) |
| 51 mm (Inner Size C) | | |
| 52 mm (Inner Size C) | | |
| 53 mm (Inner Size C) | | |
| 54 mm (Inner Size C) | | |
| 55 mm (Inner Size C) | | |
| 57 mm (Inner Size C) | | |
| 58 mm (Inner Size C) | | |
| 60 mm (Inner Size D) | .Outer Size D (28 mm I.D.) (Mates with 60, 62, 64, 66, 68, 70, 72 mm shells), or .Outer Size D (32 mm I.D.) (Mates with | .Outer Size D (Mates with 60, 63 mm shells) |
| 62 mm (Inner Size D) | | |
| 63 mm (Inner Size D) | | |
| 64 mm (Inner Size D) | | |
| 66 mm (Inner Size D) | | |
| 68 mm (Inner Size D) | | |
| 70 mm (Inner Size D) | | |

-continued

| Shell Component 10 (Outer diameter size in mm) | First Inner Component 20 (For a bipolar provisional) | Second Inner Component 30 (For a unipolar provisional) |
|---|---|---|
| 72 mm (Inner Size D) | 60, 62, 64, 66, 68, 70, 72 mm shells) | |

.mm = Millimeters
.I.D. = Inner diameter of first inner component 20

The present invention enables selective attachment of two different styles of inner provisional components with a common outer provisional shell component. The two different styles of inner components are adapted and styled for two different types of surgical procedures. While this invention has been described and exemplified, in terms of a particularly advantageous embodiment, those skilled in the art can appreciate that modification can be made without departing from the spirit and scope of this invention.

We claim:

1. A set of provisional prosthesis instrumentation to test the proper fit of an implant for either a bipolar or a unipolar hip prosthesis surgical procedure, comprising an outer shell component, a first inner component, and a second inner component different from the first inner component, and wherein the outer shell component includes an exterior surface and an interior surface, and wherein the exterior surface of the outer shell component includes a substantially hemispherical portion to enable joint articulation about the exterior surface of the outer shell component, and wherein the first inner component includes an exterior surface which is shaped to correspondingly mate with the interior surface of the shell component and an interior surface having a first configuration therein, and wherein the second inner component includes an exterior surface which is shaped to correspondingly mate with the same interior surface of the shell component and an interior surface having a second configuration therein different from the first configuration of the first inner component, and wherein one of either the first inner component or the second inner component is selectively inserted into the outer shell component in mating contact with the interior surface of the shell component, and wherein the interior surface of the first inner component comprises a substantially hemispherical surface therein which enables joint articulation about the interior surface of the first inner component, and wherein the interior surface of the second inner component comprises only a substantially nonhemispherical surface therein which prevents joint articulation about the interior surface of the second inner component, and wherein when the first inner component is selectively inserted into the outer shell component, articulation is possible about both the exterior surface of the outer shell component and about the interior surface of the first inner component, whereas when the second inner component is selectively inserted into the outer shell component, articulation is only possible about the exterior surface of the outer shell component.

2. The set of provisional prosthesis instrumentation of claim 1 wherein the shell component includes a plurality of slots therethrough.

3. The set of provisional prosthesis instrumentation of claim 2 wherein the set further includes a handle means for selective attachment to the shell component.

4. The set of provisional prosthesis instrumentation of claim 1 wherein the cross-sectional shapes of the interior surface of the shell component and the exterior surfaces of both the first and second inner components are substantially U-shaped.

5. The set of provisional prosthesis instrumentation of claim 1 wherein the exterior surface of the outer shell component comprises at least a hemispherical portion of a sphere.

6. The set of provisional prosthesis instrumentation of claim 1 wherein the substantially nonhemispherical surface is a substantially cylindrical surface.

7. The set of provisional prosthesis instrumentation of claim 1 wherein the set further includes a plurality of shell components of varying sizes, a plurality of first inner components of varying sizes, and a plurality of second inner components of varying sizes.

8. The set of provisional prosthesis instrumentation of claim 1, wherein the substantially nonhemispherical surface is a truncated cone-shaped surface.

9. A set of provisional prosthesis instrumentation for use during a trial fitting of either a bipolar prosthesis or a unipolar prosthesis for a hemiarthroplasty surgical procedure, wherein the set comprises an outer provisional shell, a first inner component, and a second inner component having a different configuration from the first inner component, and wherein the outer shell component includes an exterior surface, which comprises a substantially hemispherical portion to enable joint articulation thereabout, and an interior surface, and wherein each of the first and second inner components comprises an exterior surface which is shaped to correspondingly mate with the interior surface of said outer shell component, and wherein the first inner component includes a substantially hemispherical articulating surface, and wherein the first inner component is selectively inserted into the outer shell component for use during the trial fitting of the bipolar prosthesis to provide trial dual joint articulation about the substantially hemispherical portion of the outer shell component and about the substantially hemispherical articulating surface of the first inner component, and wherein the second inner component further includes an interior surface and wherein the second inner component is selectively inserted into the outer shell component for use during trial fitting of the unipolar prosthesis to provide trial single joint articulation only about the substantially hemispherical portion of the outer shell component only and wherein joint articulation is prevented about the interior surface and the exterior surface of the second inner component.

10. The set of provisional prosthesis instrumentation of claim 9 wherein the set further includes a plurality of shell components of varying sizes, a plurality of first inner components of varying sizes, and a plurality of second inner components of varying sizes.

11. A set of provisional hip instrumentation to test the proper fit of an implant for either a bipolar or a unipolar hip prosthesis surgical procedure, comprising an outer shell component, a first inner component, and a second inner component different from the first inner component, and wherein the outer shell component includes an exterior surface and an interior surface, and wherein the exterior surface of the outer shell component includes a substantially hemispherical portion to enable joint articulation about the exterior surface of the outer shell component, and wherein the first inner component includes an exterior surface which is shaped to correspondingly mate with the interior surface of the shell component and an interior surface which comprises a substantially hemispherical surface therein which enables joint articulation about the interior surface of the first inner component, and wherein the second inner component includes an exterior surface which is shaped to correspondingly mate with the same interior surface of the shell component and an interior surface which comprises only a nonhemispherical surface therein which prevents joint articulation about the interior surface of the second inner component and wherein this nonhemispherical surface is either a truncated cone-shaped surface or a substantially cylindrical surface, and wherein either the first inner component or the second inner component is selectively inserted into the outer shell component in mating contact with the interior surface of the shell component, and wherein when the first inner component is selectively inserted into the outer shell component, articulation is possible about both the exterior surface of the outer shell component and about the interior surface of the first inner component, whereas when the second inner component is selectively inserted into the outer shell component, articulation is only possible about the exterior surface of the outer shell component.

12. A set of provisional prosthesis instrumentation comprising an outer shell component, a first inner component, and a second inner component different from the first inner component, and wherein the outer shell component includes an exterior surface and an interior surface, and wherein the first inner component includes an exterior surface which is shaped to correspondingly mate with the interior surface of the shell component and an interior surface having a first configuration therein, and wherein the second inner component includes an interior surface which is shaped to correspondingly make with the interior surface of the shell component and an interior surface having a second configuration therein different from the first configuration of the first inner components, and wherein one of either the first inner component or the second inner component is selectively inserted into the outer shell component in mating contact with the interior surface of the shell component, and wherein the shell component includes a plurality of slots therethrough, and wherein the set further includes a handle means for selective attachment to the shell component, and wherein the shell component further includes a central threaded hold therein, and wherein the handle means includes a threaded tip for engagement with the threaded hole when the handle means is attached to the shell component.

13. A set of provisional prosthesis instrumentation for use during a trial fitting of either a bipolar prosthesis or a unipolar prosthesis for a hemiarthroplasty surgical procedure, wherein the set comprises an outer provisional shell, a first inner component, and a second inner component having a different configuration from the first component, and wherein the outer shell component includes an exterior surface, which comprises a substantially hemispherical portion, and an interior surface, and wherein each of the first and second inner components comprises an exterior surface, which is shaped to correspondingly mate with the interior surface of the outer shell component, and wherein the first inner component includes a substantially hemispherical articulating surface, and wherein the first inner component is selectively inserted into the outer shell component for use during the trial fitting of the bipolar prosthesis to provide trial dual joint articulation about the substantially hemispherical portion of the outer shell component and about the substantially hemispherical articulating surface of the first inner component, and wherein the second inner component is selectively inserted into the outer shell component for use during trial fitting of the unipolar prosthesis to provide trial single joint articulation about the substantially hemispherical portion of the outer shell component only, and wherein the shell component further includes a central threaded hole and wherein the second inner component includes a threaded post protruding from the exterior surface of the second inner component for selectively, threadably mating with the central threaded hole.

* * * * *